United States Patent [19]

Quadro

[11] Patent Number: 5,055,488

[45] Date of Patent: Oct. 8, 1991

[54] 3-METHYL-3-(4-ACETYLAMINOPHENOXY)-2,4-DIOXABENZOCYCLOHEXANONE-1 AND A PHARMACEUTICAL COMPOSITION CONTAINING THE SAME

[75] Inventor: Giuseppe Quadro, Milan, Italy

[73] Assignee: Medea Research S.r.l., Milan, Italy

[21] Appl. No.: 81,564

[22] Filed: Jul. 31, 1987

Related U.S. Application Data

[63] Continuation of Ser. No. 822,928, Jan. 27, 1986, abandoned, which is a continuation of Ser. No. 658,453, Oct. 9, 1984, abandoned, which is a continuation of Ser. No. 440,006, Nov. 8, 1982, abandoned.

[30] Foreign Application Priority Data

Nov. 24, 1981 [IT] Italy ............................... 25244/81[U]
Oct. 15, 1982 [IT] Italy ............................... 23733/82[U]

[51] Int. Cl.$^5$ .................. A61K 31/365; C07D 319/08
[52] U.S. Cl. ..................................... 514/452; 549/274
[58] Field of Search ............................... 549/274, 452

[56] References Cited

U.S. PATENT DOCUMENTS 3,431,293  3/1969  Robertson ..................... 560/66
3,674,843  7/1972  Shen et al. ..................... 560/138
3,674,844  7/1972  Shen et al. ..................... 560/138

OTHER PUBLICATIONS

C. Ruchardt et al, Liebigs Ann. Chem. (1974), pp. 15–23.
Paris et al, J. Med. Chem. (1980), vol. 23, pp. 79–82.

*Primary Examiner*—Glennon H. Hollrah
*Assistant Examiner*—Mark W. Russell
*Attorney, Agent, or Firm*—Bierman and Muserlian

[57] ABSTRACT

3-Methyl-3-(4-acetylaminophenoxy)-2,4-dioxabenzocyclohexanone-1, having formula I

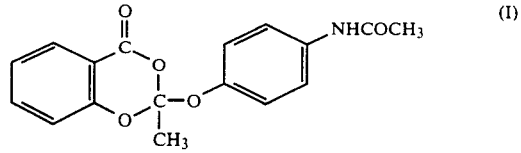

exhibits an high analgesic, antiinflammatory and antipiretic activity along with a prolonged action and an excellent gastric and systemic tolerability.

3 Claims, No Drawings

3-METHYL-3-(4-ACETYLAMINOPHENOXY)-2,4-DIOXABENZOCYCLOHEXANONE-1 AND A PHARMACEUTICAL COMPOSITION CONTAINING THE SAME

This is a continuation of application Ser. No. 822,928 filed Jan. 27, 1986 now abandoned, which is a continuation of application Ser. No. 658,453 filed Oct. 9, 1984, now abandoned which is a continuation of application Ser. No. 440,006 filed Nov. 8, 1982 now abandoned.

The present invention relates to a novel compound endowed with interesting therapeutic activities, namely 3-methyl-3-(4-acetylaminophenoxy)-2,4-dioxabenzocyclohexanone-1, having formula I

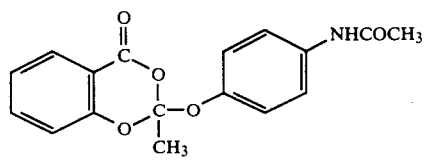

The present invention also relates to pharmaceutical compositions having analgesic, antiinflammatory and antipiretic activity containing compound (I) as active agent.

According to the invention, this compound is obtained by reaction of acetylsalicylic acid chloride (II) with 4-acetylaminophenol (III), in presence of proton acceptors (preferably tertiary amines), at temperatures from 10° to 40° C., preferably from 15° and 30° C., according to the following scheme.

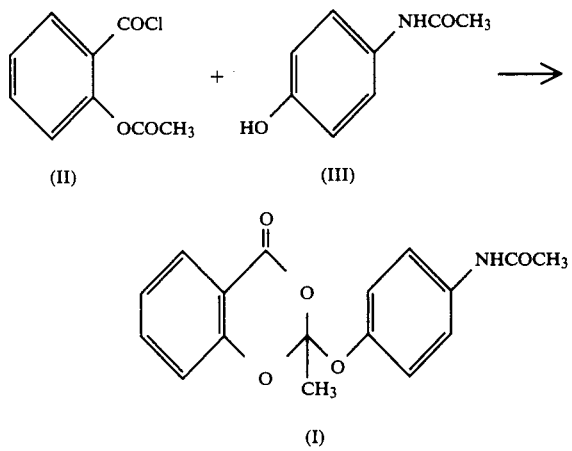

The following example illustrates the process by which the compound of the present invention is prepared.

EXAMPLE 4-acetylaminophenol (2,3 g, 0.15 moles) is added to a solution of acetylsalicylic chloride (30 g, 0.15 moles) in chloroform (120 ml).

Pyridine (12 ml, 0.15 moles) is added dropwise under vigorous stirring, keeping the reaction temperature at 20°-25° C. The reaction mixture is left at room temperature for 15 hours. The solution is washed twice with water and three times with a 5% NaOH solution. The organic phase, dried on magnesium sulphate, is evaporated.

The residue so obtained is treated many times with a toluene: ethylacetate 70:30 mixture. The solid so obtained is filtered with suction: 13 g of white crystals, m.p. 102°-105° C.

Compound (I) so obtained, hereinafter also defined with the abbreviation MR 897, is practically insoluble in water, soluble in alcohols and in halohydrocarbons.

Elementrary analysis: $C_{17}H_{15}NO_5$ (M.W.=313.3): Calculated: C=65.16%, H=4.78%; N=4.46%. Found: C=65.07%; H=4.83%; N=4.39%.

I.R. spectrum (recorded in $CH_2Cl_2$): 1680 $cm^{-1}$ (co amide), 1710 $cm^{-1}$ (co carboxylic).

$H^1$-N.M.R. spectrum (recorded in $CDCl_3$, internal standard TMS): 1.8δ(s, 3H, O—C—$CH_3$); 2δ(s, 3H, CO—$CH_3$); 6.7-8δ(m, 8H, aromatics); 8.5δ(s, 1H, NH mobile).

The therapeutic use of the two starting materials for the compound of the invention, i.e., acetylsalicylic acid and 4-acetylaminophenol (known as paracetamol) is known. In respect to them, the novel compound MR 897 has the advantage of a ready and more prolonged absorption and of an enhanced analgesic, antiinflammatory and antipiretic activity, along with total lack of the typical acetylsalicylic adid's ulcerogenic effect. A similar activity of the acetylsalicylate of 4-acetylaminophenyl (known as Benorilate) is also known. In respect to this drug, the compound according to the invention has the advantages of a higher bioavailability by the oral route, which is the preferred administration form for this kind of drug, and of a more favourable pharmacokinetics.

Particularly, MR 897 exhibits a more gradual and more prolonged absorption than both acetylsalicylic acid and 4-acetylaminophenol and, lastly, acetylsalicylate of 4-acetylaminophenyl. This prolonged effect is probably due to the particular compactness of the MR 897 molecule, which is stable even at very low pH's values, and to the lack of ionizable polar groups: from this last factor probably depends also the complete lack of gastric damaging activity.

Pharmacology

MR 897 exhibits analgesic, antiinflammatory and antipiretic activity.

In comparison with the administration of equiponderant doses of benorilate, MR 897 shows higher or comparable activities in addition to a longer duration of effect.

Acute Toxicity

The acute toxicity of MR 897 has been carried out in mice and rats administering single doses by the oral route.

Benorilate has been used as a reference standard in the same experimental conditions.

The $LD_{50}$ values have been calculated according to the method of Litchfield and Wilcoxon (J. Pharm. Exp. Therap., 1949, 96, 99).

According to the results obtained, outlined in Table 1, MR 897 has a very low acute toxicity comparable to that of Benorilate in the used experimental conditions.

TABLE 1

| Acute toxicity of MR 897 and Benorilate | | | |
|---|---|---|---|
| | | $LD_{50}$ (mg/kg) | |
| SPECIES | ROUTE | MR 897 | BENORILATE |
| mouse | os | 2300 | 2150 |
| rat | os | 3500 | 3500 |

Pharmacological Activity

Antiinflammatory Activity

The antiinflammatory activity of MR 897 and of benorilate as reference compound has been assessed by the test of the edema induced by carrageenin according to the method of Winter et al. (Proc. Soc. Exp. Biol. Med. 1962, III, 544).

The compounds under examination have been administered at the same weight doses by oral route 30 minutes before the subplantar carrageening injection.

The results obtained showed an excellent antiinflammatory activity with marked edema inhibition already at the 2nd hour and also significantly present 24 hours after the administration.

MR 897 proved to be more active than the reference compound, with statistical significance ($p<0.001$) higher than that of benorilate ($p<0.01$) in the used experimental conditions.

TABLE 2

Antiinflammatory activity of MR 897 - Carrageenin edema

| Treatment | Doses mg/kg | Animals Nr | Volume of the paw ml/10 - M ± SE | | | | | | AREA Δ% M ± SE | % inhibition compared to controls |
|---|---|---|---|---|---|---|---|---|---|---|
| | | | Basal | 2 h | 4 h | 6 h | 8 h | 24 h | | |
| Controls | — | 10 | 44.3 ± 1.0 | 70.7 ± 2.7 | 80.5 ± 2.6 | 75.1 ± 2.5 | 71.4 ± 2.6 | 56.3 ± 1.8 | 316.3 ± 31.8 ** | — |
| Benorilate | 200 | 10 | 42.5 ± 1.4 | 59.4 ± 1.3 | 61.3 ± 2.2 | 64.2 ± 2.6 | 63.2 ± 2.3 | 45.5 ± 2.4 | 197.5 ± 14.5 *** | 37.56 |
| MR 897 | 200 | 10 | 43.5 ± 1.0 | 57.1 ± 1.5 | 59.4 ± 1.9 | 60.1 ± 1.3 | 59.0 ± 1.4 | 48.1 ± 0.9 | 160.8 ± 19.9 | 49.16 |
| T Student | + p 0.05 ++ p 0.01 +++ p 0.001 | | | | | | | | | |

Analgesic Activity

The analgesic properties of MR 897 have been studied by the test of whriting induced by phenylquinone in the mouse according to the method of Siegmund E. et al. (Proc. Soc. Exp. Biol. Med., 1957, 95, 729): MR 897 has been administerd by oral route 30 minutes before the phenylquinone injection; benorilate has been used as reference standard at equiponderant doses. The results obtained are reported in Table 3.

MR 897 showed, in the used experimental conditions, an analgesic activity slightly higher than that of benorilate.

TABLE 3

Analgesic activity of MR 897 - Whriting by phenylquinone

| Treatment | Doses mg/kg os | Weight g x ± s.e. | N° whritings x ± s.e. | % inhibitions compared to controls | N° with whriting/ Total N° |
|---|---|---|---|---|---|
| Controls | — | 26.6 ± 0.58 | 19.7 ± 3.50 | — | 10/10 |
| MR 897 | 200 | 25.5 ± 0.59 | 3.5 ± 1.93 | 82.2 | 8/10 |
| Benoorilate | 200 | 25.0 ± 0.61 | 4.8 ± 1.97 | 75.6 | 9/10 |

Antipiretic Acitivity

The antipiretic activity of MR 897 has been assessed in hyperthermic rats by yeast according to the method of Boissier J. R., Simon P. (Therapie, 1962, 17, 1225).

The rats with clear hyperthermia have been treated by oral route with MR 897 and, for comparison, with benorilate at equiponderant doses.

The results obtained, reported in the Table 4, point out a good antipiretic activity of MR 897, comparable to that of benorilate in the used experimental conditions.

TABLE 4

Antipiretic activity of MR 897 - Hyperthermia by yeast in the rat

| Treatment | Doses mg/kg os | Temperature °C. x ± s.e. | | | | | | % inhibition compared to hyperth. cont. |
|---|---|---|---|---|---|---|---|---|
| | | 0 | 1 h | 2 h | 3 h | 4 h | 5 h | |
| Normal controls | — | 37.2 | 36.4 ± 0.24 | 36.18 ± 0.22 | 36.18 ± 0.22 | 36.26 ± 0.34 | 36.54 ± 0.29 | 100 |
| Hyperthermic controls | — | 39.0 | 38.08 ± 0.26 | 38.15 ± 0.26 | 38.35 ± 0.18 | 38.28 ± 0.15 | 38.20 ± 0.21 | — |
| Benorilate | 200 | 39.2 | 37.1 ± 0.51 | 36.52 ± 0.47 | 36.35 ± 0.48 | 36.72 ± 0.38 | 36.77 ± 0.33 | 81.1 |
| MR 897 | 200 | 39.0 | 37.25 ± 0.20 | 36.75 ± 0.23 | 36.69 ± 0.16 | 36.58 ± 0.11 | 37.05 ± 0.24 | 72.73 |

Gastrolesive Activity

The effect of MR 897 and, for comparison, of benorilate and acetylsalicylic acid on the gastric mucosa has been evaluated by administering the products under examination by oral route in equiponderant doses in rats fasting since at least 18 hours.

The exam of the animals' mucosa, carried out 7 hours after treatments, showed that the product MR 897 has a very low gastrolesive action, clearly lower than acetylsalicylic acid and comparable to benorilate in in the used experimental conditions.

TABLE 5

| gastrolesive action of MR 897 in Wistar rats | | |
|---|---|---|
| Treatment | Doses mg/kg | Ulcus score (mm) x ± s.e. |
| Controls | — | 0.0 ± 0.0 |
| Benorilate | 200 | 3.26 ± 1.32 |
| ASA | 200 | 15.50 ± 4.35 |
| MR 897 | 200 | 3.00 ± 0.84 |

Pharmacokinetics

The study has been carried out on female cynomolgus monkeys, weighing an average of 2.2 kg, according to a cross-over design, by administering to the same animals with a 15 days wash-out period both benorilate and MR 897.

Benorilate and MR 897 have been administered per os at the dose of 200 mg/kg to the animals fasting since the preceding evening. Since the weight of the two substances is the same, the dose is at the same time equimolar. The blood drawings were performed at the following times:

Hours: 0.5—1—2—3—4—6—8—10—24

The evaluation of plasma levels of salicylic acid has been performed by HPLC, with an HP 1084 B chromatograph provided with automatic inlet system and with UV/VIS variable wave length detector.

The average values of the average plasma levels obtained are shown in the Table 6.

TABLE 6

Plasma levels of salicylic acid after administration by oral route of MR 897 and benorilate, both at the dose of 200 mg/kg in the monkey (equiponderant and equimolar dose).
Average values in ug/ml of plasma

| Time | Levels of salicylic acid after administration of: | |
|---|---|---|
| | MR 897 | Benorilate |
| 0.5 | 30.1 | 35.0 |
| 1 | 59.6 | 68.3 |
| 2 | 88.7 | 96.5 |
| 3 | 98.1 | 108.4 |
| 4 | 102.6 | 69.3 |
| 6 | 110.4 | 42.6 |
| 8 | 112.8 | 21.8 |
| 10 | 71.9 | 9.4 |
| 24 | 1.8 | 1.6 |

From the same results, the area under the curve (AUC) has been calculated, which turned out to be the following:

AUC of MR 897 = 1440.6 $\mu g/ml^{-1} \cdot h$

AUC of benorilate = 597.8 $\mu g/ml^{-1} \cdot h$

As it is possible to verify, the considerable advantages of MR 897 in comparison with benorilate become apparent.

a) a considerably better bioavailability ratio of MR 897 about 2.5 times higher than that of benorilate, as from relative equation:

$$\frac{1440.6}{597.8} = 2.41 \text{ in favour of MR 897};$$

= 2.41 in favour of MR 897;

b) an equally better trend of the pharmacokinetic curve expressed in salicylic acid concentrations from which it turns out that benorilate reaches a peak at about the third hour, to decrease thereafter rapidly, with minimal levels at about the tenth hour, while MR 897 provides a plateau from the third, to the eighth hour, decreasing thereafter almost parallely with benorilate, but allowing high concentrations even after the tenth hours.

Such behaviour, supported by pharmacodynamics data clearly show that MR 897 can be considered a compound endowed with prolonged activity, such as to allow a considerable decrease of the administrations' frequency in comparison with benorilate, spectrum and clinical efficacy being equal.

Toxicity After Repeated Administration

The toxicity after repeated administrations (from 4 to 24 weeks) has been studied in the rabbit, in the rats and in the dog.

Tests on Rabbits

Bourgogne Tawny rabbits of both sexes, divided in three groups, have been treated for 4 consecutive weeks with MR 897 by rectal route at the doses of 150—30-0—450 mg/kg/die. A fourth group has been used as the control group. The examined parameters were: general status and behaviour; mortality; body weight; haematological and haematochemical data; urine; histopathological founds; autoptic examination; weight and histological examination of main organs. From the results obtained, there is evidence that the rectal treatment with MR 897, at the employed doses, has been well tolerated both locally and sistemically.

Tests on the Rat

Three groups of animals, males and females, have been treated by the oral route for 24 consecutive weeks with MR 897 at the following doses: 150—300—600 mg/kg/die. A fourth control group of animals has been treated only with the vehicle.

According to the considered parameters, similar to those described for the tests on the rabbit, it is possible to say that doses as high as 150-300 mg/kg are well tolerated. With higher doses (600 mg/kg) a slower body weight's increase and changes in some haematochemical data were observed.

Tests on the Dog

Beagle dogs, males and females, divided in 4 groups have been used. The compound under study has been administered, by the oral and rectal route, for 16 consecutive weeks at the doses of 250 and 500 mg/kg/die.

The considered parameters were: general status; behaviour; mortality, body weight; haematochemical and haematological data; urine; histopathological founds.

From these examinations MR 897 proved to be well tolerated in all treated groups, with the exception of the group treated by oral route with 500 mg/kg/die: those dogs, in fact, showed some changes in the haematochemical parameters.

Teratogenesis

The possible teratogenic properties of MR 897 have been examined in the rat and in the rabbit, treated by oral or subcutaneous route.

Tests on the Rat

The animals have been treated with MR 897 by oral route, at the doses of 200—400—600 mg/kg/die, from the 6th to the 16th day of pregnancy.

At the end of pregnancy, after mothers' laparatomy, the following parameters have been assessed: number of pregnant females; number of dead and alive phoetuses; number of reabsorptions; medium weight of alive phoetuses; possible somatic or scheletric deformations.

According to the obtained results, it is possible to say that the product MR 897 is without teratogenic activity. However, in the group treated with the highest dosage, a negative effect of MR 897 on the reproductive function must be pointed out. This effect results in an increase of the number of reabsorptions and a decrease of the medium body weight of the phoetuses.

Tests on the Rabbit

The animals have been treated with MR 897, from the 6th to the 18th day of pregnancy, at a dose of 300 mg/kg/die by oral or subcutaneous route.

The considered parameters, similar to those described for the rat, showed that MR 897 causes no toxic effects, in the rabbit and at the tested dose, on the mothers and on the offspring.

Tolerability

Systemic tolerability. It has been assessed in the rabbit, administering MR 897 by intraduodenal or rectal route at increasing doses up to 500 mg/kg. The considered parameters (arterial pressure, heart rate and ECG) have been assessed at different intervals after treatments. From these tests it came out that MR 897, at the tested doses, does not modify in any way the considered parameters.

The present invention also relates to all the applicable industrial aspects connected with the use of MR 897 as an analgesic, antiflammatory and antipiretic agent. Therefore, an essential aspect of the invention is represented by the pharmaceutical compositions containing predetermined quantities of MR 897.

The compounds of the present invention can be administered via the oral, rectal or topical route, in the form of tablets, granular, monodose sachets, suppositories, ointments or creams. Non limitative examples of pharmaceutical compositions are the following:

| (a) | 100 g of granular for dry syrup: | |
|---|---|---|
| | MR 897 | g 6 |
| | vanilline | g 0.100 |
| | sorbitantrioleate | g 0.500 |
| | ammonium glycirrizinate | g 0.010 |
| | flavours | g 0.050 |
| | saccharose | g 93.340 |
| | | g 50 of granular are to be reconstituted to 100 ml with water. |
| (b) | Monodose - sachets: | |
| | MR 897 | g 0.6 |
| | vanillien | g 0.010 |
| | ammonium glycirrizinate | g 0.001 |
| | saccharose | g 9.384 |
| (c) | Suppositories: | |
| | MR 897 | g 0.900 |
| | semisynthetic glycerides | g 2.5 |
| (d) | Pediatric suppositories: | |
| | MR 897 | g 0.300 |
| | semisynthetic glycerides | g 0.800 |
| (e) | Tablets: | |
| | MR 897 | g 0.600 |
| | microcrystalline cellulose | g 0.100 |
| | carboxymethylstarch | g 0.020 |
| | talc | g 0.005 |
| | magnesium stearate | g 0.005 |
| (f) | Cream for topical use: | |
| | MR 897 | g 10 |
| | natural glycerides; propylenglycol dipelargonate polyethylenglycol stearate; stabilizers deionized water | to 100 g |

I claim:

1. 3-methyl-3-(4-acetylaminophenoxy)-2,4-dioxa-benzocyclohexanone-1 having formula I

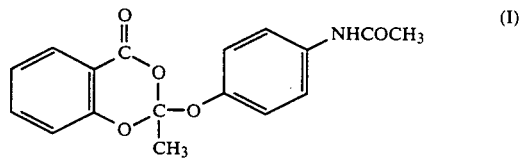

2. A pharmaceutical composition having analgesic, anti-inflammatory and anti-pyretic activities suitable for oral, rectal or topical administration containing as the principal active ingredient an effective amount of the compound according to claim 1 in combination with a pharmaceutically acceptable carrier.

3. A method for treating a patient for pain, inflammatory and pyretic conditions which comprises orally administering to said patient a composition according to claim 2.

* * * * *

UNITED STATES PATENT AND TRADEMARK OFFICE
CERTIFICATE OF CORRECTION

PATENT NO. : 5,055,488
DATED : October 8, 1991
INVENTOR(S) : GIUSEPPE QUADRO

It is certified that error appears in the above-identified patent and that said Letters Patent is hereby corrected as shown below:

On title page, item [30]

The number of the second Italian priority should read   23773 and not 23733

Signed and Sealed this

Ninth Day of March, 1993

Attest:

STEPHEN G. KUNIN

*Attesting Officer*   Acting Commissioner of Patents and Trademarks